Figure 1:
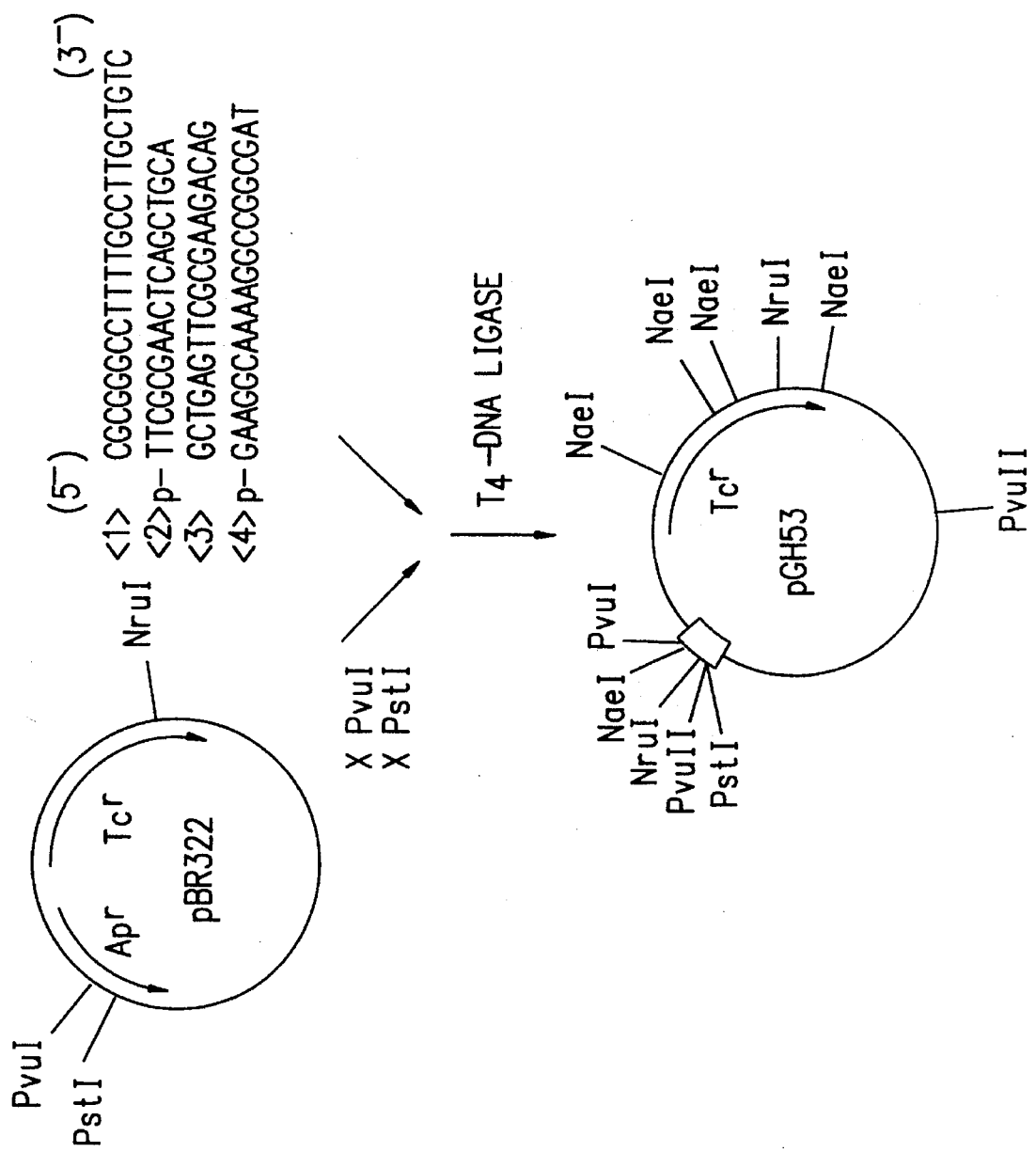

United States Patent [19]
Ohgai et al.

[11] Patent Number: 5,545,564
[45] Date of Patent: Aug. 13, 1996

[54] VECTOR FOR EXPRESSION AND SECRETION OF POLYPEPTIDE MICROORGANISM TRANSFORMED BY THE VECTOR AND PRODUCTION OF POLYPEPTIDE WITH THE SAME MICROORGANISM

[75] Inventors: Hideo Ohgai; Hiroshi Momota; Takeshi Kumakura; Noriyuki Kajifusa; Toshiki Kitazawa, all of Ako; Kazuhide Oshiden, Ibusuki; Aizo Matsushiro, Suita, all of Japan

[73] Assignee: Earth Chemical Company, Ltd., Hyogo, Japan

[21] Appl. No.: 396,282

[22] Filed: Feb. 24, 1995

Related U.S. Application Data

[63] Continuation of Ser. No. 247,604, May 23, 1994, abandoned, which is a continuation of Ser. No. 9,390, Jan. 27, 1993, abandoned, which is a continuation of Ser. No. 656,025, Feb. 15, 1991, abandoned, which is a continuation of Ser. No. 899,383, Aug. 14, 1986, abandoned which is a continuation of PCT/JP85/00696, Dec. 19, 1985.

[30] Foreign Application Priority Data

Dec. 21, 1984 [JP] Japan .................. 59-271206

[51] Int. Cl.$^6$ ............ C12N 15/70; C12N 15/62; C12N 15/18
[52] U.S. Cl. ............. 435/320.1; 536/23.4; 536/23.51
[58] Field of Search ............. 935/172.3, 320.1, 935/252.33, 252.3; 532/23.4; 536/23.1, 23.7, 23.51

[56] References Cited

U.S. PATENT DOCUMENTS 4,624,926  11/1986  Inouye et al. ............. 435/253

FOREIGN PATENT DOCUMENTS 0038182  10/1981  European Pat. Off. .
0170266  2/1986  European Pat. Off. .
8304030  11/1983  WIPO .

OTHER PUBLICATIONS

Maniatis et al. (1982), "Molecular Cloning: a Laboratory Manual", Cold Spring Harbor Lab Press, CSH, NY pp. 422 & 428.
Koshland et al. "Secretion of Beta–Lactamase Requires the Carboxy End of the Protein", *Cell*, vol. 20, pp. 749–760, Jul. 1980.
Koshland et al., "Evidence for Posttranslational Translocation of β–Lactamase Across the Bacterial Inner Membrane", *Cell*, vol. 30, pp. 893–902, Oct. 1982.
Moreno et al., "A Signal Sequence is Not Sufficient to Lead β–Galactosidase Out of the Cytoplasm", *Nature*, vol. 286, pp. 356–359, Jul. 24, 1980.
Bedoulle et al. 1980 *Nature* 285: 78–81.
Gene, vol. 12, No. 3, 4, 1980, 235–241/Elsevier/North–Holland, Biomedical Press, K. Talmadge et al..
Nucleic Acids Research, vol. 10, No. 15, 1982, 4467–4482.
Proc. Natl. Aca. Sci. USA, vol. 75, No. 8, 3737–3741, Aug. 1978.
The EMBO Journal, vol. 3, No. 10, 2437–2442, 1984.
Proc. Ntl. Aca. Sci, USA, vol. 81, 456–460, Jan. 1984.
The Journal of Biological Chemistry, vo. 259, No. 4, Issue of Feb. 25 2149–2154, 1984.

*Primary Examiner*—George C. Elliott
*Attorney, Agent, or Firm*—Spencer & Frank

[57] ABSTRACT

This present invention provides a vector for expression and secretion of a polypeptide by directly joining a DNA sequence coding for a signal peptide to a DNA sequence coding for the desired polypeptide, the vector containing the DNA sequence coding for the signal peptide, a vector for expression and secretion of the desired polypeptide as defined above and further having incorporated therein the DNA sequence coding for the desired polypeptide, a microorganism transformed by the secretion vector, and a process for producing the desired polypeptide by growing the microorganism.

1 Claim, 4 Drawing Sheets

VECTOR FOR EXPRESSION AND SECRETION OF POLYPEPTIDE MICROORGANISM TRANSFORMED BY THE VECTOR AND PRODUCTION OF POLYPEPTIDE WITH THE SAME MICROORGANISM

This is a continuation of application Ser. No. 08/247,604, filed on May 23, 1994, which is a continuation application of Ser. No. 08/009,390, filed on Jan. 27, 1993, which is a continuation application of Ser. No. 07/656,025, filed on Feb. 15, 1991, which is a continuation application of Ser. No. 06/899,383, filed on Aug. 14, 1986, all abandoned, which is a continuation of PCT/JP85/00696, filed Dec. 19, 1985.

TECHNICAL FIELD

The present invention relates to vectors for expression and secretion of a polypeptide, microorganisms transformed by the vector, and preparation of the polypeptide with use of the microorganism.

BACKGROUND ART

Processes have already been established for producing interferon, growth hormones and various other polypeptides by gene technology using host cells of *Escherichia coli, Bacillus subtilis,* yeast and the like. However, these processes, although established, have some problems still remaining to be solved, and it is not always easy to prepare polypeptides which are exactly identical with those naturally occurring. One of the most serious problems of these is that it is difficult to obtain polypeptides with an N terminus which is identical in structure to the corresponding terminus of natural products. When the genes coding for these polypeptides are to be expressed directly in host cells, the translation of the gene into the polypeptide usually takes place first at the start codon ATG, so that the polypeptide expressed has a formylmethionine residue at its N terminus. Natural polypeptides are not very likely to have formylmethionine at the N terminus, and accordingly, this method is not usable for preparing polypeptides having other N terminus. The formylmethionine residue can be removed from the polypeptide by a chemical reaction using cyanogen bromide, but when the polypeptide has other methionine residues at positions other than the N terminus, the polypeptide chain itself is cut at the position when the above method is resorted to. It is therefore impossible to obtain the desired polypeptide.

A method is also known in which the gene coding for the desired polypeptide is linked with the gene coding for some other polypeptide to express a fused polypeptide. With this method, the fusion polypeptide obtained should be treated with enzymes such as trypsin or chemically treated using cyanogen bromide to separate the desired polypeptide from the fused product. Nevertheless, if the desired polypeptide chain includes amino acid sequence which is a target for the enzyme or chemical used, the peptide chain is cut at the position of the amino acid sequence with the result that the method fails to afford the desired polypeptide. Even if the desired polypeptide can be separated from the fused polypeptide by the above method, the isolation of the desired polypeptide usually requires two purification steps, i.e., the step of separating the fused polypeptide from the resulting crude cell extract and the step of separating the desired polypeptide from the reaction mixture containing the separated fused polypeptide. These steps need cumbersome procedures and invariably result in a low yield.

Thus, the conventional genetic engineering methods encounter great difficulties in preparing polypeptides which are exactly identical with natural products. It is desired in the art to carry out research on and develop improved methods by which polypeptides which are exactly identical with those of natural origin can be prepared directly from host cells.

An object of the present invention is to provide an improved process, as desired in the art, for directly producing from host cells a polypeptide which is exactly identical with the natural one. Another object of the present invention is to provide a novel vector and a microorganism having the vector, for practicing this process.

DISCLOSURE OF THE INVENTION

The present invention provides a vector for expression and secretion of a polypeptide by directly joining a DNA sequence coding for a signal peptide to a DNA sequence coding for the desired polypeptide, the vector being characterized in that it contains the DNA sequence coding for the signal peptide, the vector containing a DNA sequence coding for a fused polypeptide comprising the DNA sequence coding for the signal peptide and the DNA sequence coding for the desired polypeptide directly joined thereto, a microorganism transformed by the vector, and a process for producing the polypeptide by growing the microorganism and collecting the polypeptide secreted therefrom.

The symbols as used herein for amino acids, nucleotides and the like are those stipulated by IUPAC or IUB or those conventional in the art, as exemplified below.

| | | | |
|---|---|---|---|
| Ser: | serine | Leu: | leucine |
| Arg: | arginine | Cys: | cysteine |
| Gln: | glutamine | Ile: | isoleucine |
| Pro: | proline | Val: | valine |
| His: | histidine | Met: | methionine |
| Ala: | alanine | Phe: | phenylalanine |
| Gly: | glycine | Asp: | aspartic acid |
| Asn: | asparagine | | |
| A: | adenine | T: | thymine |
| G: | guanine | C: | cytosine |

The term "signal peptide" refers to an amino acid sequence which acts to secrete a polypeptide produced within the cell. The polypeptides produced by all cells which are not limited to the cells of microorganisms include those remaining within the cell to perform the contemplated function and those secreted from the cell. In general, the polypeptide to be secreted from the cell is first produced within the cell in the form of a precursor which possesses a signal peptide as an N-terminal extension of more than ten to several tens of amino acid residues. The precursor then passes through the cell membrane by the aid of its signal peptide, whereupon the signal peptide is cleaved by signal peptidase, with the result that only the polypeptide free from any unnecessary amino acid residues is secreted from the cell. (The polypeptide thus screted from the cell will hereinafter be referred to as "mature polypeptide.") For example, *E. coli* β-lactamase is first produced within the cell as pre-β-lactamase, i.e. a precursor of β-lactamase with N-terminal extension of 23 amino acid residues as a signal peptide. By the aid of the signal peptide, the protein is passed through the inner membrane and secreted into the periplasm, i.e. the space between the inner membrane and the outer membrane. At this time, the signal peptide is cleaved by signal peptidase, permitting a mature polypeptide, namely active form of β-lactamase, to be accumulated in the periplasm as is already known (J. G. Sutcliffe, Proc. Natl. Acad. Sci., U.S.A., 75, 3737–3741 (1978)).

Directing attention to the characteristics of the signal peptide, we have carried out intensive research based on the concept that when host cells are caused to produce the desired foreign protein as a fused polypeptide having a signal peptide at its N terminus, the foreign protein can be secreted from the cells as a mature polypeptide, whereby the desired polypeptide can be produced easily. Consequently, we have succeeded in providing a novel vector (plasmid) which, when introduced into a host cell, actually causes the cell to secrete the desired polypeptide as a mature polypeptide, that is, a vector for expression and secretion of the polypeptide. We have also succeeded in producing the desired polypeptide using the vector.

The vector of the present invention for expression and secretion of the desired polypeptide harbors a DNA sequence coding for a signal peptide which is so designed as to have directly joined thereto a DNA sequence coding for the desired polypeptide. Accordingly, the DNA sequence coding for the desired polypeptide can be directly joined to the DNA sequence of the vector coding for the signal peptide. The expression vector thus obtained is introduced into host cells, which are then grown, whereby the desired polypeptide can be secreted or produced as a mature polypeptide outside the cells or in the periplasm.

The techinque for producing the vector of the invention will be described in detail below.

The DNA sequence coding for a signal peptide which is an essential constituent of the vector of the present invention can be any of those heretofore known and coding for signal peptides. Typical of such signal peptides is, for example, the one for the β-lactamase of *E. coli*. This signal peptide has the amino acid sequence of the formula (1) below.

```
Met - Ser - Ile - Gln - His - Phe - Arg - Val -
Ala - Leu - Ile - Pro - Phe - Phe - Ala - Ala -
Phe - Cys - Leu - Pro - Val - Phe - Ala        (1)
```

The DNA sequence coding for the signal peptide can be optionally designed because anyone of the degenerated codons for each amino acid shown below is allowable for the sequence. Each of the nucleotides may be modified by methylation or the like.

```
Met; ATG
Ser; TCT, TCC, TCA, TCG, AGT, AGC
Ile; TTT, ATC, ATA
Gln; CAA, CAG
His; CAT, CAC
Phe; TTT, TTC
Arg; AGA, AGG, CGT, CGC, CGA, CGG
Val; GTT, GTC, GTA, GTG
Ala; GCT, GCC, GCA, GCG
Leu; TTA, TTG, CTT, CTC, CTA, CTG
Pro; CCT, CCC, CCA, CCG
Cys; TGT, TGC
```

An example of especially preferred combination selected from these codons is the one represented by the formula (2) below.

```
ATGAGTATTCAACATTTCCGTGTC
GCCCTTATTCCCTTTTTGCGGCC
TTTTGCCTTCCTGTCTTCGCG        (2)
```

The DNA sequence coding for the signal peptide and possessed by the vector of the present invention basically comprises such a specific DNA sequence as exemplified above and further includes restriction endonuclease recognition sequences in the vicinity of the 3' end thereof to which a DNA sequence coding for the contemplated polypeptide is to be joined, preferably within 10-base sequence from the end, or in the DNA sequence of up to 10 bases added to the 3' end. This is essentially required for directly joining the DNA sequence coding for the desired polypeptide to the DNA sequence coding for the signal peptide. While any of the known restriction endonuclease is useful as the enzyme for recognizing the restriction endonuclease recognition sequence, preferable are those recognizing a sequence of not smaller than five bases. The DNA sequence in the vicinity of the 3' end can be altered as desired depending on the enzyme to be used.

This will be described in greater detail with reference, for example, to the signal peptide for βlactamase exemplified above. When GCC is selected as the codon for the amino acid Ala at the C terminus, the three-base sequence GGC may be linked to this sequence. The six-base sequence GCCGGC is thus formed and it can be recognized by the restriction endonuclease NaeI. The DNA sequence coding for the signal peptide is cleaved at the center of the above sequence by NaeI, whereby a DNA is obtained wherein the 3' end is GCC (corresponding to the amino acid Ala at the C end of the signal peptide). The desired DNA sequence coding for the contemplated polypeptide can be directly linked to this DNA immediately thereafter.

When TTCGCG, for example, is selected as the codons for the two-amino acid sequence Phe—Ala at the C terminus of the signal peptide, the seven-base sequence TTCGCGA can be obtained by adding adenine (A) to the 3' end. TCGCGA included in this sequence can be recognized and cleaved at the center by the restriction endonuclease NruI, giving a DNA sequence having TTCG at its 3' end. When this sequence is used in the DNA sequence coding for the signal peptide, the DNA sequence obtained by the digestion with NruI of the above DNA sequence can be linked to the DNA sequence coding for the desired polypeptic with additional two-bases, CT, CC, CA or CG, to the 5' end, whereby a DNA sequence is obtained which codes for the desired fused polypeptide.

Further if the ten-base sequence AACTCAGCTG, for example, is linked to the 3' end of the DNA sequence coding for the signal peptide, the six-base sequence CAGCTG included In the linked sequence can be recognized and cleaved at the center by PvuII, giving a DNA sequence which includes the DNA sequence coding for the signal peptide and additional seven-base sequence AACTCAG attached to the 3' end thereof. In this seven-base sequence, the first three-base sequence AAC codes for Asn, the next three-base sequence TCA codes for Set, and the last base guanine (G) can be the first base of codons for Ala, Gly, Val, Asp or Gin. Accordingly, the sequence obtained by the digestion with NruI of the above DNA sequence coding for the signal peptide, can be linked to the DNA sequence coding for a polypeptide, such as β-urogastrone, having the amino acid sequence Asn—Ser—Asp at the N terminus, when the seven-base sequence (e.g. AACTCAG) at the 5' end is removed from the latter sequence, whereby a DNA sequence can be readily obtained which codes for the desired fused polypeptide (of the signal peptide and β-urogastrone).

In addition to the DNA sequence specifically exemplified above as the DNA sequence coding for the signal peptide as a component of the vector of the present invention, another preferred example that is usable is a sequence obtained by adding a DNA sequence of up to ten bases to the above sequence. The formula (3) below represents such an example of DNA sequence having the above-mentioned ten additonal bases.

ATGAGTATTCAACATTTCCGTGTC
GCCCTTATTCCCTTTTTTGCGGCC
TTTTGCCTTCCTGTCTTCGCGAAC
TCAGCTG                                    (3)

The DNA sequence coding for the signal peptide of the present invention or DNA sequences including the sequence can be readily produced by various known methods, fop example, by a method of cutting off and isolating the sequence from the DNA of microorganisms or plasmids or the like isolated thereof, e.g. preferably pBR322 or the like, using restriction endonuclease, by a method of chemically synthesizing the DNA sequence, or by the combination of such methods. The DNA sequence coding for the signal peptide can be linked or attached to the DNA sequence coding for the desired polypeptide also by various known methods, for example, by an enzymatic reaction using $T_4$ DNA ligase or the like.

The vector of the present invention containing the DNA sequence coding for the signal peptide thus obtained can be prepared by incorporating the DNA sequence into various vectors heretofore used for cloning foreign genes, such as plasmids, vital DNA and cosmids (e.g. pJB8, Ish-Horowicz, D. and Burke, J. F., Nucleic Acids Res., 9, 2989 (1981)). Examples of suitable vectors for incorporating the DNA sequence include the above-mentioned plasmid pBR322 and the following.

* The plasmid pTUB4 (signal peptide of *Bacillus subtilis* α-amylase, H. Yamazaki et al., J. Bacteriol., 156, 327–337 (1983)).
* The plsmid pHC5 (signal peptide of *E. coli* maltose binding protein, H. Bedouelle et al., Nature, 285, 78–81 (1980)).
* The plasmid pSN518 (signal peptide of *E. coli* phosphate binding protein, K. Magota et al., J. Bacteriol., 157, 909–917 (1984)).
* The plasmid pJP12 (signal peptide of *E. coli* outer membrane pore protein which is included by phosphate limitation, N. Overbeeke et al., J. Mol. Biol., 163, 513–532 (1983)).

The DNA sequence coding for the signal peptide can be introduced into the origin vector by the same procedure as conventionally used for incorporating such foreign genes into vectors, as already exemplified.

The polypeptide secretion vector of the invention thus obtained and containing the DNA sequence coding for the signal peptide of course needs to have incorporated therein the DNA sequence coding for the desired polypeptide before being actually introduced into host cells for the expression and secretion of the desired polypeptide. In addition, the vector must contain a promoter, a ribosome binding site, a stop codon and the other regulatory DNA sequences such as terminater. In some cases, the original vector contains such factors. In such a case, the regulatory factors for expression of β-lactamase derived from the origin vector pBR322, for example, are usable as such. However, this is not a limitative example; various DNAs derived from other known microorganisms or viruses also usually contain these regulatory factors, which are therefore usable. Examples of useful factors are promoters such as those of *E. coli* lactose operon, tryptophan operon and λ phage PL, ribosome binding sites such as SD sequence of β-galactosidase, and terminaters such as λ phage 'L$^1$'. The three base sequences of TAA, TAG and TGA are usable as stop codons. Such regulatory factors can be separated by a usual method from a DNA containing them, and the desired factors can be introduced into a suitable vector by a usual method.

Examples of vectors of the present invention having especially preferred regulatory factors and the DNA sequence for signal peptide include pGH54 and pGH55 constructed from the origin vector pBR322. One of the plasmids, pGH54, has the promoter and ribosome binding site of β-lactamase and the subsequent DNA sequence coding for the signal peptide of β-lactamase. The plasmid has at the 3' end of the DNA sequence the recognition sequences for the restriction endonucleases NruI and PvuII. The characteristics of the plasmid are shown in FIG. 1, which also schematically shows the production procedure therefor.

With reference to FIG. 1, pGH54 is characterized by the illustrated restriction endonuclease cleavage map. pGH54 has about 3.9 kb as determined by 1.0% agarose gel electrophoresis. The *E. coli* strain HB101 harboring the plasmid pGH54 has been deposited with the designation "HB101 [pGH54]" and deposition number FERM BP-679 in Fermentation Research Institute, Agency of Industrial Science and Technology, MITI.

pGH55 is in common with pGH54 in that the plasmid has the promoter and the ribosome binding site of β-lactamase and the subsequent DNA sequence coding for the signal peptide of β-lactamase, but is devoid of about 0.64 kb DNA of pGH54 containing a PvuII restriction site and has another PvuII restriction site in the vicinity of the 3' end of the DNA sequence coding for the signal peptide. The characteristics of the plasmid and the outline of production procedure therefor are shown in FIG. 2.

Figure 2:
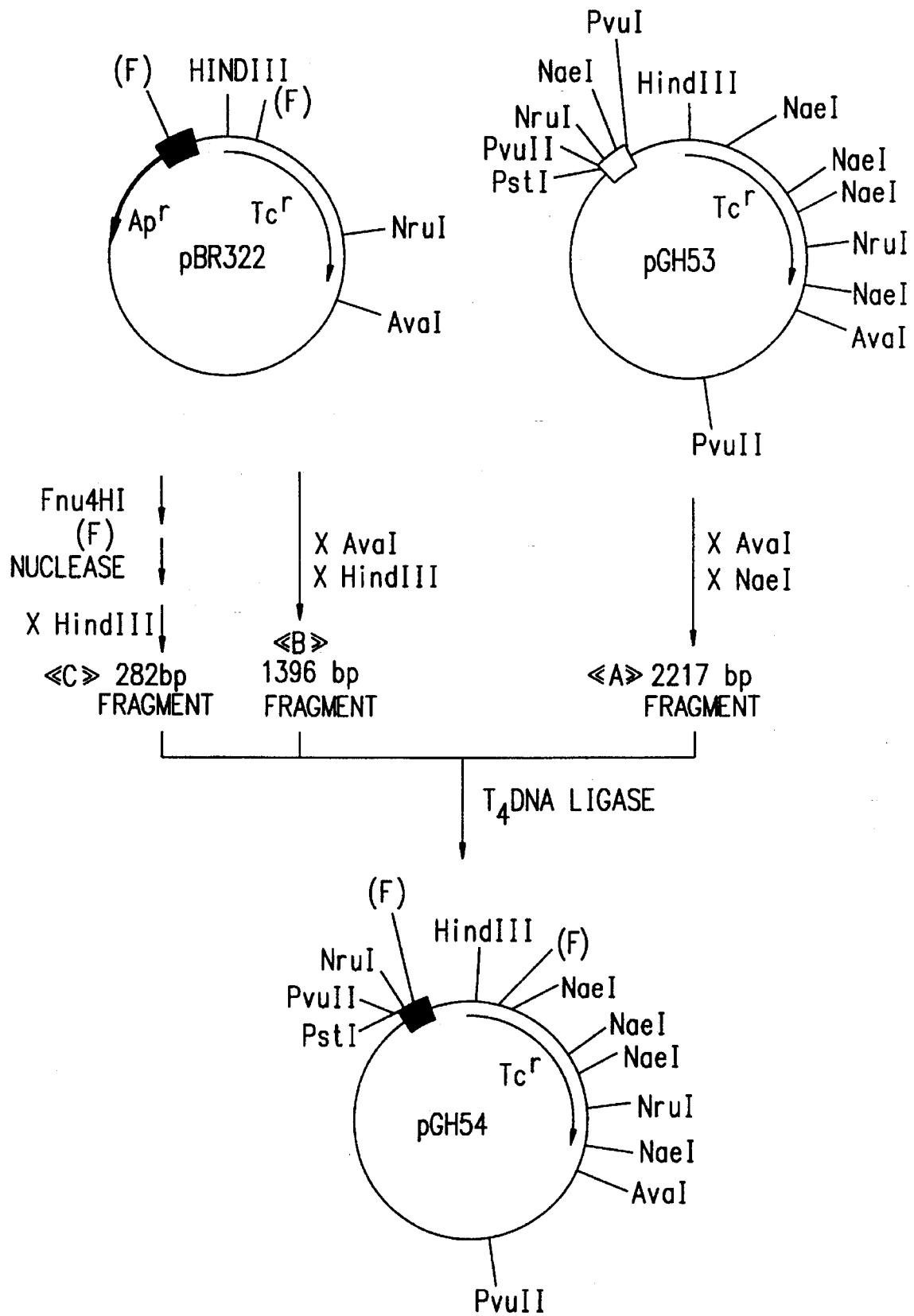

With reference to FIG. 2, pGH55 is characterized by the illustrated restriction endonuclease cleavage map and has about 3.3 kb as determined by the same method as above. The *E. coli* strain HB101 harboring the plasmid pGH55 has been deposited with the designation "HB101 [pGH55]" and deposition number FERM BP-680 in Fermentation Research Institute, Agency of Industrial Science and Technology, MITI.

The vector of the present invention for expression and secretion of the desired polypeptide contains various regulatory factors mentioned above and has the DNA sequence coding for the signal peptide and the DNA sequence directly attached thereto and coding for the desired polypeptide. This vector is constructed in the same manner as the vector of the invention described above. The invention provides this vector for expression and secretion of the desired mature polypeptide.

The polypeptide, as well as the DNA sequence thereof, to be contained in the mature polypeptide secretion vector of the present invention, as an DNA sequence attached to the DNA sequence coding for the signal peptide to code for a fused polypeptide can be any of desired polypeptides and DNA sequences coding therefor. Examples of such polypeptides are epidermal growth factor, somatostatin, insulin, GIP, R-MSA, thymosin $β_4$, growth hormone, growth hormone-releasing factor and like hormones and growth factors, interferons, interleukin 2, tumor necrosis factor and like lymphokines and immuno-regulatory substances, serum albumin, plasminogen activator, apolipoproteins and like blood constituent substances, hepatitis B virus surface antigen and like antigen proteins for vaccines, etc. The DNA sequences coding for these polypeptides may be extracted and isolated from cells or the like containing them by usual methods, or can be chemically synthesized according to the amino acid sequence of the polypeptide concerned.

Given below are examples of these polypeptides and/or the DNA sequences thereof.

○ Somatostatin

```
                Ala Gly Cys Lys Asn Phe Phe
5' AATTCATGGCTGGTTGTAAGAACTTCTTT
        GTACCGACCAACATTCTTGAAGAAA
Trp Lys Thr Phe Thr Ser Cys
TGGAAGACTTTCACTTCGTGTTGATAG
ACCTTCTGAAAGTGAAGCACAACTATCCTAG 5'
```

○ Proinsulin

```
Phe Val Asn Gln His Leu Cys Gly Ser His Leu
TTTGTGAACCAACACCTGTGCGGCTCACACCTG
Val Glu Ala Leu Tyr Leu Val Cys Gly Glu Arg
GTGGAAGCTCTCTACCTAGTGTGCGGGGAACGA
Gly Phe Phe Tyr Thr Pro Lys Thr Arg Arg Glu
GGCTTCTTCTACATACCCAAGACCCGCCGGGAG
Ala Glu Asp Leu Gln Val Gly Gln Val Glu Leu
GCAGAGGACCTGCAGGTGGGGCAGGTGGAGCTG
Gly Gly Gly Pro Gly Ala Gly Ser Leu Gln Pro
GGCGGCGGCCCTGGTGCAGGCAGCCTGCAGCCC
Leu Ala Leu Glu Gly Ser Leu Gln Lys Arg Gly
TTGGCCCTGGAGGGCTCCCTGCAGAAGCGTGGC
Ile Val Glu Gln Cys Cys Thr Ser Ile Cys Ser
ATTGTGGAACAATGCTGTACCAGCATCTGCTCC
Leu Tyr Gln Leu Glu Asn Tyr Cys Asn
CTCTACCAGCTGGAGAACTACTGCAAC
```

[Nature Vol. 282, 29, November 1979]

○ Hepatitis B virus surface antigen

```
ATGGACATTGACCCTTATAAAGAATTTGGAGCTA
CTGTGGAGTTACTCTCTCGTTTTTGCCTTCTGAC
TTCTTTCCTTCCGTACGAGATCTTCTAGATACCG
CCGCAGCTCTGTATCGGGATGCCTTAGAGTCTCC
TGAGCATTGTTCACCTCACCATACTGCACTCAGG
CAAGCAATTCTTTGCTGGGGAGACTTAATGACTC
TAGCTACCTGGGTGGGTACTAATTTAGAAGATCC
AGCATCTAGGGACCTAGTAGTCAGTTATGTCAAC
ACTAATGTGGGCCTAAAGTTCAGACAATTATTGT
GGTTTCACATTTCTTGTCTCACTTTTGGAAGAGA
AACGGTTCTAGAGTATTTGGTGTGTTTTGGAGTG
TGGATTCGCACTCCTCCAGCTTATAGACCACCAA
ATGCCCCTATCCTATCAACGCTTGCGGAGACTAC
TGTTGTTAGAGGACGAGGCAGGTCCCCTAGAAGA
AGAACTCCCTCGCCTCGCAGACGAAGATCTCAAT
CGCCGCGTCGCAGAAGATCTCAATCTCGGGAATC
TCAATGTTAG
```

○ Hepatitis B virus surface antigen

```
ATGGAGAACATCACATCAGGATTCCTAGGACCCC
TGCTCGTGTTACAGGCGGGGTTTTTCTTGTTGAC
AAGAATCCTCAGAATACCGCAGAGTCTAGACTCG
TGGTGGACTTCTCTCAATTTTCTAGGGGGAACTA
CCGTGTGTCTTGGCCAAAATTCGCAGTCCCCAAT
CTCCAATCACTCACCAACCTCCTGTCCTCCAACT
TGTCCTGGTTATCGCTGGATGTGTCTGCGGCGTT
TTATCATCTTCCTCTTCATCCTGCTGCTATGCCT
CATCTTCTTGTTGGTTCTTCTGGACTATCAAGGT
ATGTTGCCCGTTTGTCCTCTAATTCCAGGATCAT
CAACCACCAGCACGGGATCCTGCAGAACCTGCAC
GACTCCTGCTCAAGGAATCTCTATGTATCCCTCC
TGTTGCTGTACAAAACCTTCGGATGGAAACTGCA
CCTGTATTCCCATCCCATCATCCTGGGCTTTCGG
AAAATTCCTATGGGAGTGGGCCTCAGCCCGTTTC
TCTTGGCTCAGTTTACTAGTGCCATTTGTTCAGT
GGTTCGTAGGGCTTTCCCCCATTGTTTGGCTTTC
AGTTATATGGATGATGTGGTATTGGGGGCCAAGT
CTGTACAGCATCTTGAGTCCCTTTTTACCGCTGT
TACCAATTTTCTTTTGTCTTTGGGCATACATTTA
A
```

○ Epidermal growth factor

H-Asn-Ser-Tyr-Pro-Gly-Cys-Pro-Ser-Ser-Tyr-Asp-Gly-Tyr-Cys-Leu-Asn-Gly-Gly-Val-Cys-Met-His-Ile-Glu-Ser-Leu-Asp-Ser-Tyr-Thr-Cys-Asn-Cys-Val-Ile-Gly-Tyr-Ser-Gly-Asp-Arg-Cys-Gln-Thr-Arg-Asp-Leu-Arg-Trp-Trp-Glu-Leu-Arg-OH
[C. R. Savage, Jr., T. Inagami, S. Cohen, J. Biol. Chem., 247, 7612 (1972); C. R. Savage, Jr., J. H. Hash, S. Cohen, J. Biol. Chem., 248, 7669 (1973)]

○ Gastric inhibitory polypeptide

H-Tyr-Ala-Glu-Gly-Thr-Phe-Ile-Ser-Asp-Tyr-Ser-Ile-Ala-Met-Asp-Lys-Ile-Arg-Gln-Gln-Asp-Phe-Val-Asn-Trp-Leu-Leu-Ala-Gln-Gln-Lys-Gly-Lys-Lys-Ser-Asp-Trp-Lys-His-Asn-Ile-Thr-Gln-OH
[J. C. Brown, Can. J. Biochem., 49, 255 (1971); J. C. Brown et al., same, 49, 867 (1971); H. Yajima et al., J. Am. Chem. Soc., 97, 5593 (1975)]

○ Growth hormone-releasing factor

H-Val-His-Leu-Ser-Ala-Glu-Glu-Lys-Glu-Ala-OH
[A. V. Shally et al., J. Biol. Chem., 246, 6647 (1971); D. F. Veber et al., Biochem. Biophys. Res. Commun., 45, 235 (1971)]

○ Somatostatin

H-Ala-Gly-Cys-Lys-Asn-Phe-Phe-Trp-Lys-Thr-Phe-Thr-Ser-Cys-OH
[A. V. Schally et al, Fed. Proc. Fed. Ani. Soc. Exp. Biol., 34, 584 (1975); A. V. Schally et al., Biochemistry, 15, 509(1976)]

○ R-MSA (polypeptide with multiplication-stimulating activity)

H-Ala-Tyr-Arg-Pro-Ser-Glu-Thr-Leu-Cys-Gly-Gly-Glu-Leu-Val-Asp-Thr-Leu-Gln-Phe-Val-Cys-Ser-Asp-Arg-Gly-Phe-Tyr-Phe-Ser-Arg-Pro-Ser-Gly-Arg-Ala-Asn-Arg-Arg-Ser-Arg-Gly-Ile-Val-Glu-Glu-Cys-Cys-Phe-Arg-Ser-Cys-Asp-Leu-Ala-Leu-Leu-Glu-Thr-Tyr-Cys-Ala-Thr-Pro-Ala-Tys-Ser-Glu-OH
[H. Marquart, G. J. Todaro, J. Biol. Chem., 256, 6859 (1981)]

○ Somatostatin - 28

H-Ser-Ala-Asn-Ser-Asn-Pro-Ala-Met-Ala-Pro-Arg-Glu-Arg-Lys-Ala-Gly-Cys-Lys-Asn-Phe-Phe-Trp-Lys-Thr-Phe-Thr-Ser-Cys-OH
[F. Esch et al., Proc. Natl. Acad. Sci. USA., 77, 6827 (1980); N. Ling et al,, Biochem. Biophys. Res. Commun., 95, 945(1980)]

○ Thymosin $\beta_4$

Ac-Ser-Asp-Lys-Pro-Asp-Met-Ala-Glu-Ile-Glu-Lys-Phe-Asp-Lys-Ser-Lys-Leu-Lys-Lys-Thr-Glu-Thr-Gln-Glu-Lys-Asn-Pro-Leu-Pro-Ser-Lys-Glu-Thr-Ile-Glu-Gln-Glu-Lys-Gln-Ala-Gly-Glu-Ser-OH
[T. L. K. Low et al, Proc. Natl. Acad. Sci. U.S.A., 78, 1162 (1981)]

The DNA sequence for the polypeptide can be attached to the DNA sequence for the signal peptide by introducing the former sequence into the polypeptide secretion vector of the invention having the latter sequence, by the foregoing methods, for example, by an enzymatic reaction using restriction endonucleases and an enzymatic reaction using $T_4$ DNA ligase. Alternatively, the DNA base sequence coding for a fused polypeptide of the signal peptide and desired polypeptide is chemically synthesized and then introduced into a vector in the same manner as the introduction of the DNA sequence for signal peptide.

In this way, the polypeptide secretion vector of the present invention can be obtained which has the DNA sequence coding for the fused polypeptide. The vector has a promoter and ribosome binding site upstream of the DNA sequence coding for the fused polypeptide, and a stop codon immediately after the DNA sequence of the desired polypeptide constituting the above sequence. When introduced into a suitable host cell, the vector transforms the cell to express and secrete the polypeptide.

Plasmid pUG201 is a preferred example of polypeptide secretion vector. pUG201 includes the promoter and ribosome binding site of β-lactamase, the DNA sequence for signal peptide of β-lactamase, the DNA sequence for β-urogastrone (desired polypeptide) and a stop codon therefor as accurately arranged in this order. This sequence is shown in Table 4 in the example to follow. The $E.$ $coli$ strain HB101 harboring the plasmid pUG201 has been deposited with the designation "HB101 [pUG201]" and deposition number FERM BP-681 in the Fermentation Research Institute, Agency of Industrial Science and Technology, MITI.

The polypeptide secretion vector of the present invention can be introduced into host cells by various known methods. The host cell to be used is not limited specifically but can be any of various known ones. Examples of useful host cells are gram-negative bacteria such as $E.$ $coli,$ gram-positive bacteria such as $Bacillus$ $subtilis,$ actinomycetes, yeast, etc. Especially preferable among these are the strain HB101 and the other strains derived from $E.$ $coli$ K12. These host cells have signal peptidase as one of the machineries for secreting polypeptides such as extracellular proteins and outer membrane proteins which are required for maintaining the normal function of the cell. It is known that there is little or no difference in substrate specificity among the signal peptidases derived from various microorganisms. (D. Perlman and H. O. Halvorson, J. Mol. Biol., 167, 391 (1983)).

The vector can be introduced into host cells, for example, by treating the host cells in an aqueous solution containing calcium chloride at a low temperature, and adding the vector to the solution (E. Lederberg, S. and Cohen, J., Bacteriol., 119, 1072 (1974)).

When the cells thus transformed by the vector of the invention are grown, a fused polypeptide is produced within the cells, and a mature polypeptide is subsequently secreted extracellularly or into the periplasm and accumulated. Stated more specifically, mRNA is first transcribed from the gene on the vector coding for the fused polypeptide by the action of the transcription regulatory factors of the vector and various factors in the host cell. Subsequently the fused polypeptide is produced from the mRNA by the action of the translation regulatory factors and various factors in the host cell and is secreted extracellularly or into the periplasm by the aid of the signal peptide. At the same time, the signal peptide is cleaved from the fused polypeptide by signal peptidase. Consequently, a mature polypeptide which is free from the signal peptide or any other unnecessary amino acid residues is secreted and accumulated extracellularly or into the periplasm.

The mature polypeptide thus secreted and accumulated can be separated off and further purified by usual methods. The polypeptide can be separated off from the culture supernatant or from a periplasmic fraction prepared by the osmotic shock method and purified, for example, by a suitable combination of gel filtration, adsorption chromatography, ion-exchange chromatography, high performance liquid chromatography, etc. The desired polypeptide obtained according to the present invention is a secreted product and therefore has the advantage of being easy to separate off and purify.

BEST MODE OF PRACTICING THE INVENTION

The present invention will be described below in greater detail with reference to the following examples, in which the following methods and procedures were used unless otherwise specified.

1. Cleavage of DNA with restriction endonuclease

One of the reaction buffers (Table 1) prepared by diluting the concentrated buffer with water is admixed with an aqueous solution (or buffer solution) or pellet of DNA, a restriction endonuclease is then added to the mixture, and the resulting mixture is allowed to stand in a water bath at 37° C. for 3 hours for reaction. The standard amount of restriction endonuclease to be used is one unit per microgram of DNA in 10 μl of the reaction mixture.

TABLE 1

| Composition (mM) | Low salt buffer | Medium salt buffer | High salt buffer |
| --- | --- | --- | --- |
| Sodium chloride | 0 | 50 | 100 |
| Tris-HCl (pH 7.5) | 10 | 10 | 50 |
| Magnesium chloride | 10 | 10 | 10 |
| Dithiothreitol | 1 | 1 | 1 |

2. Phenol extraction

This extraction method is practiced after the completion of the enzymatic reaction to inactivate the enzyme and terminate the reaction. To the reaction mixture is added TE-saturated phenol (phenol saturated with 10 mM tris-HCl (pH 8.0) containing 1 mM EDTA) in one-half the amount of the reaction mixture, followed by full stirring and further by stirring with addition of chloroform in one-half the amount of the reaction mixture. The resulting mixture is centrifuged to collect the buffer layer containing the DNA. To the buffer layer are added 3 M sodium acetate buffer (pH 5.0) in 0.1 times the amount of the layer and cold ethanol in 2 times the amount of the same. The mixture is stirred and allowed to stand at −20° C. for at least one hour. The DNA is collected as a pellet, whereby the phenol is completely removed.

3. Preparation of blunt ended DNA with DNA polymerase I (Klenow fragment)

The DNA is dissolved in an aqueous solution containing 40 mM potassium phosphate (pH 7.4), 6 mM magnesium chloride, 1 mM β-mercaptoethanol, 1 mM ATP, and 1 mM of each of dATP, dCTP, dGTP and dTTP. DNA polymerase I (Klenow fragment, product of Takara Shuzo Co., Ltd.) is added to the solution in an amount of one unit per microgram of DNA, followed by reaction at 12° C. for 30 minutes.

4. Ligation (circularization) of DNA fragments with $T_4$ DNA ligase

The DNA fragments are ligated (circularized) by reacting the fragments with $T_4$ DNA ligase (product of Takara Shuzo Co., Ltd.) in an amount of 3 units per microgram thereof at 12° C. for at least 5 hours in an aqueous solution containing 66 mM tris-HCl (pH 7.5), 6.6 mM magnesium chloride, 10 mM dithiothreitol, 1 mM ATP, and 0.01% bovine serum albumin.

5. Method of transformation

The strain HB101 derived from *E. coli* K12 is used as the host cell.

The strain HB101 is grown in LB medium (1% bacto trypton, 0.5% bacto yeast extract and 0.5% sodium chloride) at 37° C. until an absorbance at 610 nm reaches 0.25. The culture (40 ml) is centrifuged (6000 r.p.m. for 10 minutes) to collect the cells, which are then ice-cooled. The cells are washed with 20 ml of 0.1 M magnesium chloride, suspended in 20 ml of ice-cooled solution of 0.1 M calcium chloride and 0.05 M magnesium chloride and ice-cooled for one hour, followed by centrifugation (6000 r.p.m. for 10 minutes). The cells collected are suspended again in 2 ml of 0.1 M calcium chloride and 0.05 M magnesium chloride. To a 0.2 ml portion of the suspension is added 0.01 ml of the reaction mixture of DNA fragments ligated with $T_4$ DNA ligase. The mixture is ice-cooled for one hour, then heated in a water bath at 42.5° C. for 90 seconds, and allowed to stand in a water bath at 37° C. for one hour with addition of 2.8 ml of LB medium.

The transformant to be obtained is selected by the following procedure according to antibiotic resistance, i.e. by spreading 0.3 ml portions of the reaction mixture over a plate medium prepared by adding 50 µg/ml of ampicillin or 20 µg/ml of tetracycline to LB medium containing 1.5% agar, followed by incubation at 37° C. overnight. The growing *E. coli* colonies are isolated.

6. Isolation of plasmids

The strain harboring plasmids is grown at 37° C. in 500 ml of LB medium containing 50 µg/ml of ampicillin or 20 µg/ml of tetracycline, until an absorbance at 610 nm reaches about 0.6. The culture is added to 80 mg of chloramphenicol and further incubated with shaking at 37° C. for 12 to 16 hours. The culture is centrifuged (6000 r.p.m. for 10 minutes) to collect the cells, which are then washed with 0.85% sodium chloride, suspended in 2.5 ml of solution of 20% sucrose and 50 mM tris-HCl (pH 8.0) and subsequently ice-cooled for 10 minutes with addition of 0.5 ml of 0.25 M tris-HCl (pH 8.0) containing 1% lysozyme. The mixture is further ice-cooled for 10 minutes with addition of 1 ml of 0.25 m EDTA (pH 8.0). Subsequently, 4 ml of solution of 6 mM tris-HCl (pH 8.0), 60 mM EDTA and 0.1% Triton X-100 is added to the mixture. The resutling mixture is centrifuged (25000 r.p.m. for 90 minutes) to collect the supernatant. A 9.0 g quantity of cesium chloride is dissolved in 8.2 ml of the supernatant, and 0.8 ml of 1% ethidium bromide is further added thereto. The mixture is centrifuged (2000 r.p.m. for 10 minutes) to remove the suspended matter. The solution is ultracentrifuged (50000 r.p.m. for 15 hours). The resulting product is irradiated with ultraviolet rays to separate the plasmid portion emitting fluorescence. This portion is subjected to extraction five to six times using isopropanol saturated with 5 M sodium chloride solution to remove the ethidium bromide. Finally, the portion is dialysed against 10 mM tris-HCl (pH 8.0) and 1 mM EDTA to remove the cesium chloride.

7. Synthesis of oligonucleotide

An oligonucleotide is synthesized by the following solid-phase method (solid-phase phosphotriester method). (H. Ito et al., Nucleic Acids Research, 10, 1755–1769 (1982)).

A resin prepared by aminomethylating 1% cross-linked polystyrene resin S-X1 (200 to 400 mesh, product of BIO-.RAD Laboratories) is first reacted with monosuccinic acid ester of 5'-o-dimethoxytritylnucleoside to obtain a nucleoside supporting resin. The following procedure is carried out using a DNA synthesizer produced by Bachem Inc.

The above resin (40 mg) is placed into a reactor and treated with a solution of 1 M zinc bromide in dichloromethane-isopropanol (85:15) to remove the dimethoxytrityl group at the 5' position. Next, a completely protected dinucleotide (prepared by the method of C. Broka et al., Nucleic Acids Research, 8, 5461–5471 (1980)) in the form of a triethylammonium salt (50 mg) is added to the resin, and the mixture is subjected to condensation using a condensation agent (mesitylene-5-nitrotriazole). The above procedure is repeated to successively lengthen the chain and obtain a resin having supported thereon a protected oligonucleotide. In the final condensation step, 25 mg of the triethylammonium salt of a mononucleotide prepared by the method of the above literature is used in place of dinucleotide when so required.

Next, the protected oligonucleotide is removed from the resin using a solution of 0.5 M pyridine aldoximate in pyridine-water (1:1). The removed compound is purified by a Sephadex G-50 column (2×100 cm, product of Pharmacia) and further by high performance liquid chromatography (pump: Model 6000A, product of Waters Associates, detector: Model 440 Detector, column: Micro-Bondapak $C_{18}$, eluent: (5→40%) acetonitrile-aqueous solution of triethylammonium acetate (0.1M). The compound is subsequently treated with 80% acetic acid for the removal of the protective group and subjected to high performance liquid chromatography again until a single peak is obtained. This high performance liquid chromatography is conducted under the same conditions as above except that the eluent used is (5→25%) acetonitrile-aqueous solution of triethylammonium acetate (0.1M).

8. Analysis of DNA sequence

The DNA sequence is analyzed in the following manner according to the method of Messing (M13 method, Methods Enzymol., 101, 20 (1983)). A DNA fragment is digested by one or two restriction endonucleases and separated by 1% agarose gel electrophoresis. The DNA fragment is cloned on the vector M13mp8RF (product of Pharmacia). The recombinant phage DNA obtained is used to transfect *E. coli* strain JM107 by the method of Mandel and Higa (J. Mol. Biol., 53, 154 (1970)). To 0.2 ml of the resulting cell suspension are added 25 µl of 25 mg/ml isopropyl-β-D-thiogalactoside and 40 µl of 20 mg/ml 5 -bromo-4-chloro-3-indolyl-β-D-galactoside. The suspension is then added to 3 ml of H-top agar solution (1% bacto trypton, 0.8% sodium chloride and 0.5% agar) solubilized and maintained at 50° C. The mixture is spread over a plate of 2xTY medium (1.6% bacto trypton, 1% yeast extract and 0.5% sodium chloride) solidified by addition of 1.5% agar and incubated overnight at 37° C. The recombinant phage having the DNA fragment inserted therein produces a colorless plaque, whereas the parent strain M13mp8 produces a blue plaque. The desired recombinant phage is therefore easily selectable.

One of the colorless plaques is collected by a Pasteur pipette and added to 1 ml of 2xTY medium along with 0.01 ml of culture of JM103 strain, followed by incubation with shaking at 37° C. for about 5 hours to proliferate the recombinant phage. The resulting culture is centrifuged to remove the cell, 0.2 ml of 20% polyethylene glycol 6000 is admixed with the supernatant, and the mixture is allowed to stand at room temperature for at least 15 minutes and thereafter centrifuged. The phage sediment is collected, from which a single stranded DNA is extracted using phenol. The extract is used as a template single stranded DNA.

The template single stranded DNA and a primer (M13 15-base primer, product of Takara Shuzo Co., Ltd.), each in an amount of 0.5 pmol, are mixed together, heated at 60° C. for 20 minutes and then slowly cooled. To the mixture are then added 2 μl of [$\alpha^{32}$P]-dCTP (400 Ci/mmol, product of Pharmacia) and 2 units of DNA polymerase I (Klenow fragment, product of Takara Shuzo Co., Ltd.). After thoroughly stirring the mixture, 3.2 μl portions thereof are placed into reaction tubes containing four kinds of dNTP-ddNTP mixtures listed in Table 2 individually in an amount of 2 μl. Each of the mixtures is reacted at room temperature for 20 minutes, and further reacted for 20 minutes with addition of chase reaction solution (1 mM of each of dATP, dCTP, dGTP and dTTP). To the reaction mixture is added 6 μl of formamide stop solution (95% v/v formamide, 0.1% xylene cyanol and 0.1% bromophenol blue). The mixture is heated at 95° C. for 3 minutes and then rapidly cooled. Subsequently, a 2 μl portion of the sample is electrophoresised on 6% or 8% polyacrylamide gel (1800 V, 30 mA, 2–3 hours), and the gel is transferred to filter paper (Whatman 3MM), dried in a dryer and autoradiographed to read to DNA sequence.

TABLE 2

| Composition of dNTP-ddNTP mixture (μl) | | | | |
|---|---|---|---|---|
| | A | C | G | T |
| 0.5 mM dGTP | 20 | 15 | 1 | 20 |
| 0.5 mM dATP | 1 | 15 | 20 | 20 |
| 0.5 mM dTTP | 20 | 15 | 20 | 1 |
| 100 mM tris-HCl (pH 7.5) + 1 mM EDTA | 20 | 15 | 20 | 20 |
| H$_2$O | 45 | 45 | 50 | 30 |
| | (ddA) | (ddC) | (ddG) | (ddT) |
| 1.0 mM ddNTP | 15 | 15 | 10 | 30 |
| Total | 121 | 120 | 121 | 121 |

In Table 2, ddA stands for dideoxyadenosine, ddC for dideoxycytidine, ddG for dideoxyguanosine and ddT for dideoxythymidine.

9. Agarose gel electrophoresis

Agarose gel electrophoresis, as well as separation of DNA fragments from the resulting gel, is conducted according to the method described in the manual of Schleif and Wensink ("Practical Methods in Molecular Biology" (1981), Springer-Verlag, pp. 114–125), using the power supply of Atto Corporation, Consta power Model SJ1065, a plastics water container, 12×15 cm (equipped with platinum electrodes), as the electrophoresis apparatus, Agarose I (product of Dojin Chemical Lab.) and 40 mM tris-HCl (containing 5 mM sodium acetate and 1 mM EDTA, pH 7.9) as the electrophoresis buffer.

10. Polyacrylamide gel electrophoresis

Polyacrylamide gel electrophoresis and separation of DNA fragments from the resulting gel are conducted according to the methods described in the above manual, pp. 78–87 and pp. 114–125. The electrophoresis is conducted using the power supply of Atto Corporation, Consta power Model SJ1065, the electrophoresis apparatus of the same company, Model SJ11060SD, an aqueous solution of acrylamide and N,N'-methylenebisacrylamide (29:1) as the acrylamide solution, N,N,N',N'-tetramethylethylenediamine as a polymerization accelerator, ammonium persulfate as a polymerization catalyst and 90 mM tris-borate buffer (pH 8.3) containing 2.5 mM EDTA as the electrophoresis buffer.

Example 1

Construction of mature polypeptide secretion vectors pGH54 and pGH55

(A) Construction of intermediate plasmid pGH53

1) Four kinds of oligonucleotides having the following sequences were synthesized by the foregoing solid-phase phosphotriester method in order to obtain a part of the DNA sequence of the signal peptide of E. coli β-lactamase.

| [1] 5' - | CGCCGGCCTTTTGCCTTCCTGTC - 3' |
|---|---|
| [2] | TTCGCGAACTCAGCTGCA |
| [3] | GCTGAGTTCGCGAAGACAG |
| [4] | GAAGGCAAAAGGCCGGCGAT |

The 5' ends of the oligonucletides [2] and [4] were phosphorylated with T$_4$ polynucleotidekinase (product of Bethesda Research Labolatories). More specifically, 10 μg of each of these oligonucleotides was dissolved in 50 μl of 50 mM tris-HCl (pH 9.5) containing 10 mM magnesium chloride, 5 mM dithiothreitol and 1 mM ATP, 5 units of T$_4$ polynucleotidekinase was added to the solution, the mixture was reacted at 37° C. for 30 minutes, and the nucleotide was subjected to phenol extraction to terminate the reaction.

2) The plasmid pBR322 (Bolivar et al., Gene, 2, 95–113 (1977)) was used as a cloning vector.

Ten μg of plasmid pBR322 was digested in the high salt buffer using restriction endonucleases PstI (product of Takara Shuzo Co., Ltd.) and PvuI (product of New England Biolabs). The fragments were electrophoresised on 1.0% agarose gel to isolate a DNA fragment of about 4.24 kb.

3) The DNA fragment obtained in 2) above was combined with the phosphorylated oligonucleotides [2] and [4] prepared in 1) and the unphosphorylated oligonucleotides [1] and [3] (each about 1 μg) and reacted with T$_4$ DNA ligase for ligation. HB*101* strain derived from E. coli K-12 was transformed with the resulting reaction mixture. The desired plasmid pGH53 was isolated from one clone selected from among the tetracycline-resistant transformants obtained.

FIG. 1 schematically shows the series of steps.

FIG. 1 shows the process for preparing the plasmid pGH53 by insertion of the synthetic oligonucleotides [1], [2], [3] and [4] in the origin vector pBR322, and also the characteristics of pGH53. The rectangular block shown represents the DNA sequence originated from the synthetic oligonucleotides.

The plasmid pGH53 obtained was found to have a size of 4.3 kb by 1.0% agarose gel electrophoresis. Analysis by the M13 method revealed that the DNA sequence of the plasmid was devoid of the sequence between PstI and PvuI restriction sites of pBR322 and had, in place of this sequence, the oligonucleotides [1], [2], [3] and [4] inserted as shown below.

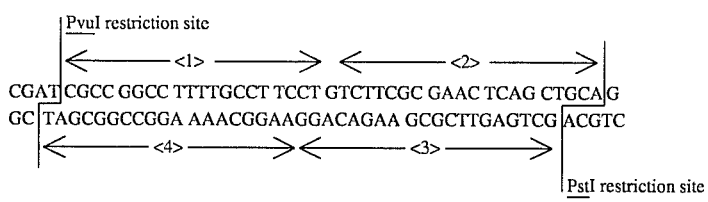

The plasmid pGH53 has been deposited with the designation "HB101 [pGH53]" and deposition number FERM BP-678 in Fermentation Research Institute, Agency of Industrial Science and Technology, MITI.

(B) Construction of mature polypeptide secretion vector pGH54

1) Ten μg of plasmid pGH53 obtained in (A) was digested in the medium salt buffer using the restriction endonucleases NaeI (product of New England Biolabs) and AvaI (product of Takara Shuzo Co., Ltd.). The fragments were electrophoresised on 1.0% agarose gel to isolate a DNA fragment ((A)) of about 2.22 kb.

The fragment contains a major portion of the DNA sequence derived from the synthetic oligonucleotides and the replication origin of the plasmid.

2) Plasmid pBR322 was digested in the medium salt buffer using the restriction endonucleases AvaI and HindIII (products of Takara Shuzo Co., Ltd.). The fragments were electrophoresised on 1.0% agarose gel to obtain a DNA fragment ((B)) of about 1.40 kb.

The fragment contains part of the promoter and the whole structural gene of tetracycline resistance gene.

3) Twenty μg of plasmid pBR322 was digested in the low salt buffer using the restriction endonuclease Fnu4HI (product of New English Biolabs). Subsequently, the cohesive ends of the DNA fragments were removed with S1 nuclease, by dissolving the DNA, after phenol extraction, in 1 ml of buffer (pH 4.5) containing 6 mM sodium acetate, 40 mM sodium chloride and 1 mM zinc sulfate, adding 2,000 units of S1 nuclease (product of Bethesda Research Laboratories) and incubating the mixture at 20° C. for 30 minutes. Next, the DNA, after phenol extraction, was digested in the medium salt buffer using the restriction endonuclease HindIII, followed by 6% polyacrylamide gel electrophoresis to obtain a DNA fragment ((C)) of about 0.28 kb.

The fragment contains the promoter and ribosome binding site of β-lactamase, part of a gene coding for the signal peptide thereof, and part of the promoter of a tetracycline-resistant gene.

4) The three fragments ((A)), ((B)) and ((C)) obtained were ligated using $T_4$ DNA ligase. HB101 strain was transformed with the resulting reaction mixture. The desired plasmid pGH54 was isolated from one clone selected from among the tetracycline-resistant transformants obtained.

The DNA sequence analysis of pGH54 by the M13 method revealed that the plasmid had the promoter and ribosome binding site of β-lactamase, a DNA sequence coding for the signal peptide thereof, and restriction sites for NruI and PvuII upstream and downstream from the 3' end of this sequence, respectively.

FIG. 2 schematically shows the series of the foregoing steps.

FIG. 2 is a diagram showing the process for preparing the polypeptide secretion vector pGH54 of the present invention from pGH53 and pBR322, and the characteristics of the vector pGH54 obtained. The solid rectangular block shown represents the DNA sequence coding for the signal peptide.

As already mentioned, pGH54 has a size of about 3.9 kb and is characterized by the restriction endonuclease map shown in FIG. 2. The DNA sequence analysis by the M13 method revealed that the plasmid had the DNA sequence coding for β-lactamase signal peptide as shown by the formula (3).

(C) Construction of mature polypeptide secretion vector pGH55

1) The following procedure was executed to prepare pBRH02 which is a derivative of pBR322 lacking a region between the AvaI and PvuII restriction sites. Five μg of pBR322 was digested in the medium salt buffer with the restriction endonucleases AvaI and PvuII (product of Takara Shuzo Co., Ltd.). The fragments were subjected to phenol extraction and then made blunt-ended with DNA polymerase I (Klenow fragment, product of Takara Shuzo Co., Ltd.). The fragments were electrophoresised on 1.0% agarose gel to isolate a DNA fragment of about 3.72 kb, which was then circularized with $T_4$ DNA ligase. HBH101 strain was transformed with the resulting reaction mixture. The desired plasmid pBRH02 was isolated from one clone selected from among the ampicillin- and tetracycline-resistant transformants obtained. Unlike pBR322, the plasmid pBRH02 obtained was digested neither by AvaI nor by PvuII.

2) Five μg of pBRH02 obtained by the procedure 1) was digested in the medium salt buffer using the restriction endonucleases PstI and BamHI (products of Takara Shuzo Co., Ltd.). The fragments were then electrophoresised on 1.0% agarose gel to isolate a DNA fragment ((D)) of about 2.60 kb.

The fragment contains part of a tetracycline-resistant gene and the replication origin of the plasmid.

3) Ten μg of pGH54 was digested in the medium salt buffer with the restriction endonucleases PstI and BamHI, and the fragments obtained were electrophoresised on 1.0% agarose gel to isolate a DNA fragment ((E)) of about 0.66 kb.

The fragment contains the promoter and ribosome binding site of β-lactamase, part of a DNA sequence coding for the signal peptide thereof and part of a tetracycline-resistant gene.

4) The two fragments ((D)) and ((E)) obtained were ligated with $T_4$ DNA ligase. HB101 strain was transformed with the resulting reaction mixture. The desired plasmid pGH55 was isolated from one clone selected from among the tetracycline-resistant transformants obtained.

Figure 3:
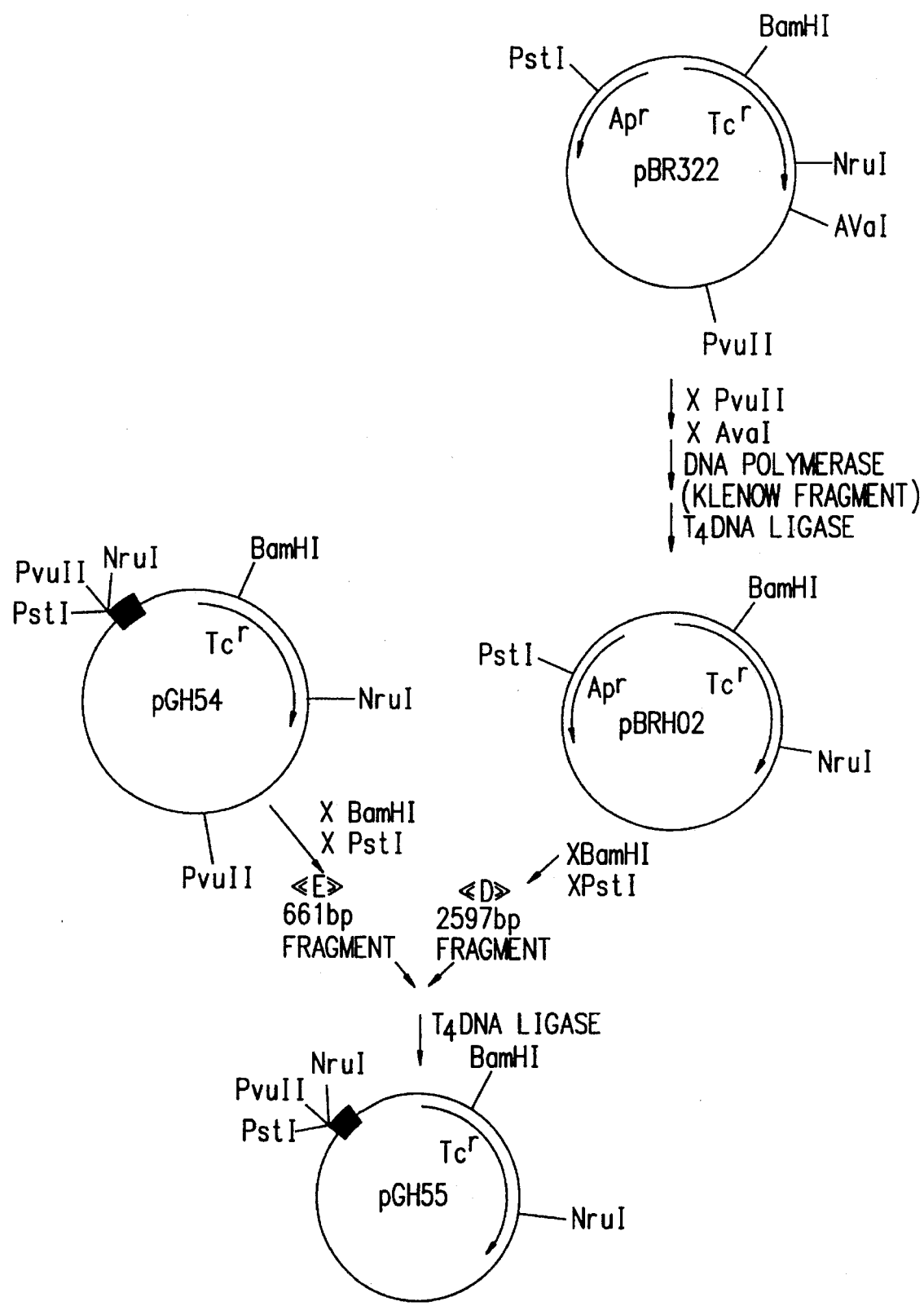

FIG. 3 shows the series of steps schematically.

FIG. 3 is a diagram showing the process for preparing the polypeptide secretion vector pGH55 of the invention from pGH54 and pBRH02 which was obtained from pBR322, and the characteristics of pGH55.

pGH55 is characterized by the restriction endonuclease map of FIG. 3 and was found to have a size of about 3.3 kb by 1.0% agarose gel electrophoresis. The DNA sequence analysis of pGH55 by the M13 method revealed that the plasmid was similar to pGH54 except that it was devoid of part of the DNA sequence of pGH55 having about 0.64 kb and including a PvuII restriction site and that another PvuII restriction site thereof was present in the vicinity of the 3' end of the DNA sequence coding for a signal peptide.

Example 2

Construction of secretion vector having DNA sequence coding for signal peptide-β-urogastrone fused polypeptide (A) Synthesis of DNA sequence coding for β-urogastrone With reference to the amino acid sequence reported by H. Gregory (Nature, 257, 325–327 (1975)), the DNA sequence shown in Table 3 below was constructed, the sequence comprising a DNA sequence coding for β-urogastrone, a start codon and a stop codon and restriction endonuclease recognition sites added to the front and rear thereof. This DNA sequence is disclosed in Japanese Patent Application SHO 59-137691 already filed by the present inventors.

TABLE 3

| |
|---|
| 5'  AAT TCG AAG ATC TGC ATG AAT AGC |
| 3'           GC TTC TAG ACG TAC TTA TCG |
| GAT TCT GAG TGC CCA CTG TCT CAC |
| CTA AGA CTC ACG GGT GAC AGA GTG |
| GAT GGC TAT TGT CTG CAC GAC GGT |
| CTA CCG ATA ACA GAC GTG CTG CCA |
| GTT TGC ATG TAC ATC GAA GCT TTG |
| CAA ACG TAC ATG TAG CTT CGA AAC |
| GAT AAA TAC GCG TGT AAC TGT GTA |
| CTA TTT ATG CGC ACA TTG ACA CAT |
| GTG GGT TAT ATC GGT GAA CGC TGT |
| CAC CCA ATA TAG CCA CTT GCG ACA |
| CAA TAC CGT GAT CTG AAA TGG TGG |
| GTT ATG GCA CTA GAC TTT ACC ACC |
| GAA TTG CGT TAA TGA AGA TCT |
| CTT AAC GCA ATT ATC ACT TCT AGA |
| G           3' |
| CCT AG  5' |

(B) Construction of plasmid having DNA sequence coding for β-urogastrone

1) Ten μg of pBR322 was first digested in the high salt buffer with EcoRI (product of Takara Shuzo Co., Ltd.) and BamHI, and the fragments were electrophoresised on 1.0% agarose gel to isolate a DNA fragment of about 3.99 kb.
2) The DNA fragment obtained by the step 1) was ligated to the DNA sequence coding for β-urogastrone obtained by the process (A) using T₄ DNA ligase. HB101 strain was transformed by the resulting reaction mixture. Plasmid was isolated from one clone selected from among the ampicillin-resistant transformants obtained. Thus, the plasmid pUG3 was obtained which contained the DNA sequence for β-urogastrone between the EcoRI and the BamHI sites of pBR322.

The strain HB101 harboring the plasmid pUG3 has been deposited with the designation "HB101 [pUG3]" and deposition number FERM BP-543.

(C) Construction of pUG201 pUG3 obtained by the process (B) was digested with the restriction endonuclease HinfI, and the resulting DNA fragment was inserted into pGH55 at the PvuII restriction site thereof to obtain an secretion vector, pUG201, containing a DNA sequence coding for the fused polypeptide of signal peptide and β-urogastrone. This process is as follows.

1) pUG3 (15 μg) was digested in the high salt buffer with HinfI (product of Takara Shuzo Co., Ltd.). The fragments were subjected to phenol extraction and made blunt-ended with DNA polymerase (Klenow fragment). Subsequently, the fragments were electrophoresised on 6% polyacrylamide gel to isolate a DNA fragment ((F)) of about 0.43 kb.

The fragment was found to contain the DNA sequence (inclusive of a stop codon) coding for β-urogastrone except the seven bases at the 5' end.

2) pGH55 contains a DNA sequence which comprises a sequence coding for the signal peptide of β-lactamase and the following seven-base sequence coding for the N-terminal region of β-urogastrone and which is so designed as to be cleaved with the restriction endonuclease PvuII immediately after the seven-base sequence. Five μg of pGH55 was digested in the medium salt buffer with PvuII to obtain a DNA fragment ((G)) of about 3.26 kb.

The fragment has all genetic information of pGH55.

3) About one μg of fragment ((F)) obtained by the step 1) was ligated to about 0.5 μg of fragment ((G)) obtained by the step 2) with T₄ DNA ligase. HB101 strain was transformed with the resulting reaction mixture. The desired plasmid pUG201 was isolated from one strain selected from among the tetracycline-resistant transformants obtained.

Figure 4:
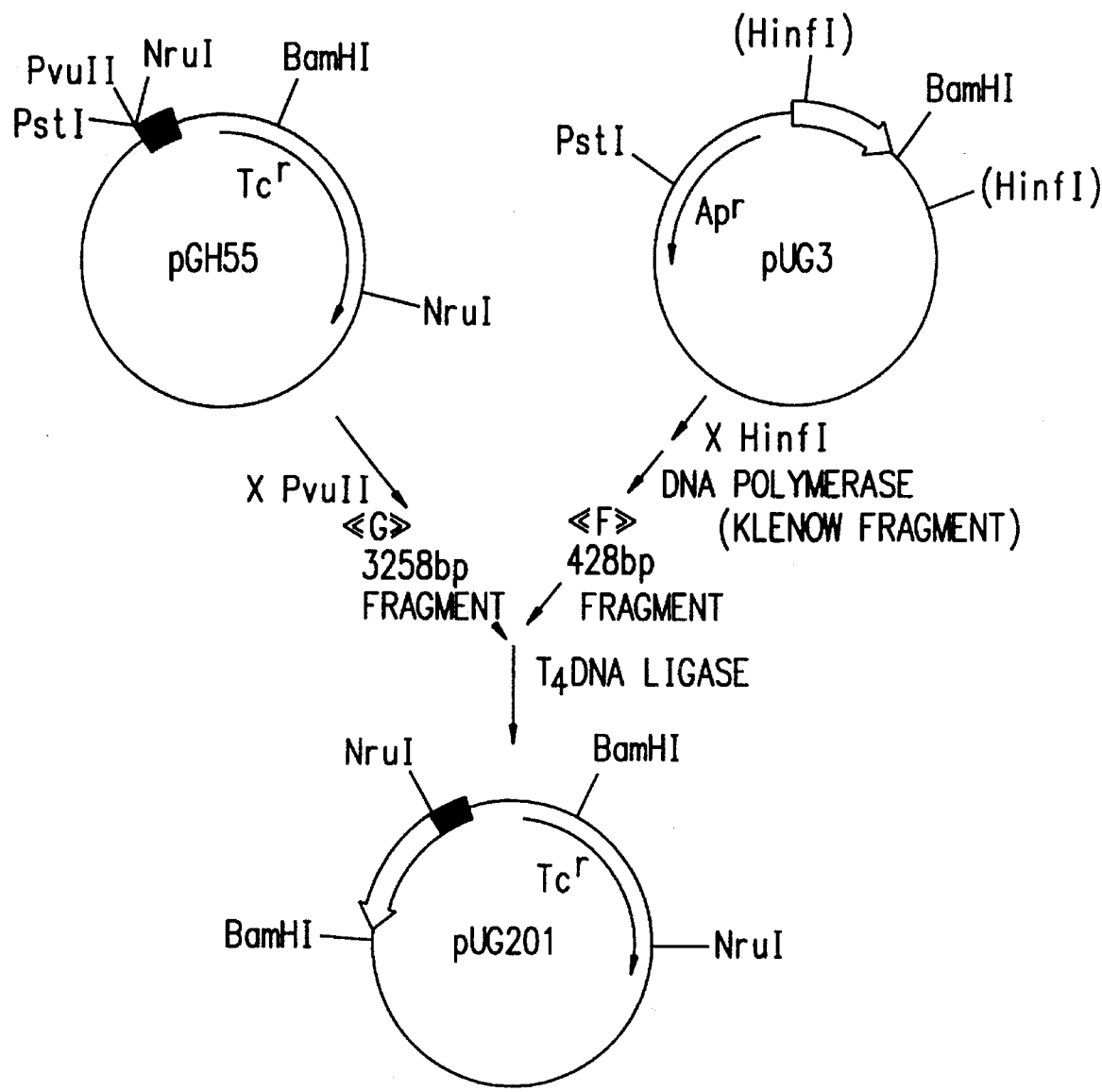

FIG. 4 schematically shows the series of steps.

FIG. 4 is a diagram showing the process for preparing pUG201 from pGH55 and pUG3. pUG201 is the polypeptide secretion vector of the present invention which contains a DNA sequence coding for the fused polypeptide of signal peptide and desired polypeptide (β-urogastrone). The blank arrow shown represents the gene of β-urogastrone.

pUG201 was found to have a size of about 3.7 kb by 1.0% agarose gel electrophoresis. When cleaved with BamHI or Hind III, the vector provides two kinds of DNA fragments. This indicates that pUG201 contains the gene of β-urogastrone. The size of the fragments checked shows that pUG201 is the desired plasmid. The part of the DNA sequence of pUG201 from the promoter region of β-lactamase to the β-urogastrone gene inclusive was analysed by the M13 method. Table 4 below shows the DNA sequence identified, indicating that pUG201 contains the promoter, ribosome binding site, DNA sequence coding for β-lactamase signal peptide and for β-urogastrone (DNA sequence coding for the fused polypeptide) as arranged accurately in this order. Table 4 also shows the amino acid sequence corresponding to the DNA sequence.

The E. coli strain HB101 harboring pUG201 has been deposited with the designation "HB101 [pGH201]" and deposition number FERM BP-681 in Fermentation Research Institute, Agency of Industrial Science and Technology, MITI.

TABLE 4

TTCTTGAAGACGAAAGGGCCTCGTGATACGCCT
AAGAACTTCTGCTTTCCCGGAGCACTATGCGGA

ATTTTTATAGGTTAATGTCATGATAATAATGGT
TAAAAATATCCAATTACAGTACTATTATTACCA

TTCTTAGACGTCAGGTGGCACTTTTCGGGGAAA
AACAATCTGCAGTCCACCGTGAAAAGCCCCTTT

┌─
TGTGCGCGGAACCCCTATTTGTTTATTTTTCTA
ACACGCGCCTTGGGGATAAACAAATAAAAAGAT

TABLE 4-continued

```
─────── Promoter ───────
AATACATTCAAATATGTATCCGCTCATGAGACA
TTATGTAAGTTTATACATAGGCGAGTACTCTGT

─────┐
ATAACCCTGATAAATGCTTCAATAATATTGAAA
TATTGGGACTATTTACGAAGTTATTATAACTTT
```

```
     /Ribosome binding site
AAGGAAGAGT   ATG  AGT  ATT  CAA  CAT
TTCCTTCTCA   TAC  TCA  TAA  GTT  GTA
             Met  Ser  Ile  Gln  His TTC  CGT  GTC  GCC  CTT  ATT  CCC  TTT
AAG  GCA  CAG  CGG  GAA  TAA  GGG  AAA
Phe  Arg  Val  Ala  Leu  Ile  Pro  Phe
              Signal peptide TTT  GCG  GCC  TTT  TGC  CTT  CCT  GTC
AAA  CGC  CGG  AAA  ACG  GAA  GGA  CAG
Phe  Ala  Ala  Phe  Cys  Leu  Pro  Val TTC  GCG  AAC  TCA  GAT  TCT  GAG  TGC
AAG  CGC  TTG  AGT  CTA  AGA  CTC  ACG
Phe  Ala  │Asn  Ser  Asp  Ser  Glu  Cys CCA  CTG  TCT  CAC  GAT  GGC  TAT  TGT
GGT  GAC  AGA  GTG  CTA  CCG  ATA  ACA
Pro  Leu  Ser  His  Asp  Gly  Tyr  Cys
         β-Urogastorone polypeptide CTG  CAC  GAC  GGT  GTT  TGC  ATG  TAC
GAC  GTG  CTG  CCA  CAA  ACG  TAC  ATG
Leu  His  Asp  Gly  Val  Cys  Met  Tyr ATC  GAA  GCT  TTG  GAT  AAA  TAC  GCG
TAG  CTT  CGA  AAC  CTA  TTT  ATG  CGC
Ile  Glu  Ala  Leu  Asp  Lys  Tyr  Ala TGT  AAC  TGT  GTA  GTG  GGT  TAT  ATC
ACA  TTG  ACA  CAT  CAC  CCA  ATA  TAG
Cys  Asn  Cys  Val  Val  Gly  Tyr  Ile GGT  GAA  CGC  TGT  CAA  TAC  CGT  GAT
CCA  CTT  GCG  ACA  GTT  ATG  GCA  CTA
Gly  Glu  Arg  Cys  Gln  Tyr  Arg  Asp CTG  AAA  TGG  TGG  GAA  TTG  CGT  TAA
GAC  TTT  ACC  ACC  CTT  AAC  GCA  ATT
Leu  Lys  Trp  Trp  Glu  Leu  Arg │

TAGTGAAGATCTGGATC
ATCACTTCTAGACCTAG
```

Example 3

Expression and secretion of mature β-urogastrone by *E. coli* harboring pUG201

(A) Growing HB101 strain harboring pUG201

A modified culture medium of the following composition was used.

| Modified E medium (composition per liter) | |
|---|---|
| Magnesium sulfate.7H$_2$O | 0.2 g |
| Citric acid.1H$_2$O | 2.0 g |
| Potassium phosphate, dibasic (anhydrous) | 10.0 g |
| Sodium ammonium hydrogenphosphate.4H$_2$O | 3.5 g |
| Glucose | 2.0 g |
| Casamino acid | 1.0 g |

| Modified E medium (composition per liter) | |
|---|---|
| L-Proline | 0.23 g |
| L-Leucine | 39.5 mg |
| Thiamine hydrochloride | 16.85 mg |
| Tetracycline hydrochloride | 20.0 mg |

HB101 harboring pUG201 was precultured and 1 ml of the culture was inoculated into a flask containing 200 ml of the modified E medium and incubated with shaking at 37° C. for 24 hours.

(B) Extraction of periplasmic fraction and cytoplasmic fraction from cells

The culture obtained by the procedure (A) was centrifuged (6000 r.p.m. for 10 minutes) to collect the cells, which were washed with a buffer (10 mM tris-HCl and 30 mM sodium chloride, pH 8.0) in 0.5 times the amount of the culture. A periplasmic fraction was extracted from the washed cells by the osmotic shock method (H. C. Neu and L. A. Heppel, J. B.C., 240, 3685–3692 (1965)). For the extraction, one g of wet cells were suspended in 80 ml of 30 mM tris-HCl buffer (pH 8.0) containing 20% sucrose. With addition of 0.32 ml of 0.25 M EDTA (pH 8.0), the suspension was agitated in a rotary shaker at 24° C. and 180 r.p.m. for 10 minutes and then centrifuged (9000 r.p.m. for 10 minutes) to collect the cells. Subsequently, the cells were resuspended in 80 ml of water cooled with ice. The suspension was allowed to stand in ice for 10 minutes with occasional stirring and centrifuged (9000 r.p.m. for 10 minutes) to obtain a supernatant separated from the cells. The supernatant obtained is the periplasmic fraction.

The cells separated from the periplasmic fraction was washed with the same washing buffer as above and then suspended in 6 ml of PBS (20 mM sodium phosphate (pH 7.0) containing 150 mM sodium chloride). The suspension was treated by a sonicator (Model 5202, product of Ohtake Works Co., Ltd.) at an output of 100 W three times, for 30 seconds each time, and centrifuged (18000 r.p.m. for 20 minutes) to obtain a supernatant, which was a cytoplasmic fraction.

(C) Determination of β-urogastrone by radioimmunoassay

The fractions obtained by the procedure (B) were checked for the presence of β-urogastrone by β-urogastrone specific radioimmunoassay. The assay was conducted by the following method. Rabbits were immunized with purified human β-urogastrone as an antigen to obtain antiserum. The β-urogastrone (300 μg) was dissolved in 0.2 ml of distilled water, 1.5 ml of 50% polyvinylpyrrolidone was added to the solution, and the mixture was stirred for 2 hours at room temperature. Complete Freund's adjuvant (2.0 ml) was added to the mixture to obtain an emulsion, which was subcutaneously injected into the chest portion of three rabbits. After repeating the immunization four times every two weeks, 50 μg of the antigen was further intravenously injected, the whole blood was collected 3 days thereafter, and the serum was separated.

Next, the following assay conditions were determined in view of the titration curve for determining the dilution degree of the antiserum for the assay, incubation time for optimizing the assay conditions, method of separating the antibody-bound labeled antigen (bound) from the free labeled antigen (free), and etc.

The diluting solution used was a 10 mM phosphate buffer (pH 7.4) containing 0.5% of bovine serum albumin (BSA), 140 mM sodium chloride and 25 mM disodium EDTA. The diluting solution (400 μl), 100 μl of the sample or standard human β-urogastrone and 100 μl of antihuman β-urogastrone serum were mixed together. After the mixture was incubated for 24 hours at 4° C., 100 μl of $^{125}$I-labeled human β-urogastrone solution (about 5000 cpm) was added to the mixture. After the mixture was further incubated for 48 hours at 4° C., 100 μl of second antibody (antirabbit γ-globulin goat serum, 1:20), 100 μl of normal rabbit serum (1:200) and 900 μl of 10 mM PBS buffer containing 5% polyethylene glycol were added to the resulting mixutre, followed by incubation at 4° C. for 3 hours. The mixture was centrifuged at 3000 r.p.m. for 30 minutes, the supernatant was separated off, and the precipitate was counted. The content of immunoreactive substance as human β-urogastrone in the sample was determined from the standard curve obtained with use of standard human β-urogastrone.

The results are shown in Table 5. Also shown in Table 5 are the results achieved by HB101 transformants incorporating pGH55 or pUG3 and similarly prepared.

TABLE 5

| | β-Urogastrone immunoreactivity | |
|---|---|---|
| Strain | Periglasmic fraction | (μg/liter culture) Cytoplasmic fraction |
| HB101 [pGH55] | <0.03 | <0.03 |
| HB101 [pUG3] | <0.03 | <0.03 |
| HB101 [pUG201] | 263 | 0.62 |

Table 5 reveals that although substantially no β-urogastone immunoreactive substance is detected from the extract of the *E. coli* strain (HB101[pGH55]) harboring a plasmid containing the DNA sequence coding for a signal peptide only or of the *E. coli* strain (HB101[pUG3]) having a plasmid containing the DNA sequence coding for β-urogastrone only, remarkable β-urogastrone immuno-reactivity is detected from the extract of *E. coli* strain (HB101[pUG210]) harboring the mature polypeptide secretion vector of the invention which contains a DNA sequence coding for the fused polypeptide of signal peptide and β-urogastrone, and a promoter and ribosome binding site linked to the upstream of the sequence.

The result obtained by growing the microorganism transformed by the vector of the present invention indicates that the β-urogastrone immunoreactive substance is almost entirely (99.8%) distributed in the periplasm. This shows that β-urogastrone is secreted into the periplasm through the cell membrane according to the present invention utilizing the DNA sequence of the fused polypeptide of signal peptide and β-urogastrone.

(D) Purification of polypeptide

The β-urogastrone immunoreactive substance in the periplasmic extract was purified until a single polypeptide was obtained, by adsorption chromatography using Butyl-Toyopearl (product of Toyo Soda Mfg. Co., Ltd.), ion-exchange chromatography using CM-Toyopearl (product of Toyo Soda Mfg. Co., Ltd.) or high performance liquid chromatography using a PepRPC column (product of Pharmacia).

The polypeptide purified was found to be identical with the purified β-urogastrone isolated from human urine, by all the results of polyacrylamide gel electrophoresis, SDS-polyacrylamide gel electrophoresis, amino acid analysis and N-terminal analysis.

We claim:
1. A vector for expression and secretion of β-urogastrone which is pUG201.

* * * * *